United States Patent [19]
Hibbard

[11] Patent Number: 5,859,891
[45] Date of Patent: *Jan. 12, 1999

[54] AUTOSEGMENTATION/AUTOCONTOURING SYSTEM AND METHOD FOR USE WITH THREE-DIMENSIONAL RADIATION THERAPY TREATMENT PLANNING

[76] Inventor: Lyn Hibbard, 16 Tealbrook Dr., St. Louis, Mo. 63141

[ * ] Notice: This patent issued on a continued prosecution application filed under 37 CFR 1.53(d), and is subject to the twenty year patent term provisions of 35 U.S.C. 154(a)(2).

[21] Appl. No.: 813,701

[22] Filed: Mar. 7, 1997

[51] Int. Cl.$^6$ .................................................. G01N 23/04
[52] U.S. Cl. .............................. 378/62; 378/65; 382/131; 382/132; 600/427
[58] Field of Search ........................... 128/922; 600/427; 382/131, 132; 378/58, 62, 65

[56] References Cited

U.S. PATENT DOCUMENTS

| | | | |
|---|---|---|---|
| 4,751,643 | 6/1988 | Lorensen et al. | 364/414 |
| 4,764,971 | 8/1988 | Sullivan | 382/9 |
| 4,791,567 | 12/1988 | Cline et al. | 364/413.13 |
| 4,856,074 | 8/1989 | Nagaoka | 382/22 |
| 4,961,425 | 10/1990 | Kennedy et al. | 128/653 R |
| 5,072,384 | 12/1991 | Doi et al. | 382/132 |
| 5,133,020 | 7/1992 | Giger et al. | 382/6 |
| 5,166,876 | 11/1992 | Cline et al. | 364/413.13 |
| 5,185,809 | 2/1993 | Kennedy et al. | 382/6 |
| 5,187,658 | 2/1993 | Cline et al. | 364/413.13 |
| 5,204,625 | 4/1993 | Cline et al. | 324/306 |
| 5,239,591 | 8/1993 | Ranganath | 382/6 |
| 5,289,374 | 2/1994 | Doi et al. | 364/413.13 |

(List continued on next page.)

FOREIGN PATENT DOCUMENTS

96/42070 12/1996 WIPO .

OTHER PUBLICATIONS

Delagnes et al., Active Contours Approach to Object Tracking in Image Sequences with Complex Background, *Pattern Recognition Letters*, vol. 16(2), pp. 171–178 (1995).

(List continued on next page.)

*Primary Examiner*—David P. Porta
*Assistant Examiner*—David Vernon Bruce
*Attorney, Agent, or Firm*—Hale and Dorr LLP

[57] ABSTRACT

An autosegmentation/autocontouring method that may be used for quickly and accurately contouring the regions and boundaries around regions for the development of cross-sections that may be linearly disposed for the three-dimensional reconstruction of an image is described and claimed. The autosegmentation/autocontouring method includes at least four steps. The first step is to digitize a CT, MRI, or other suitable image and display it on a display screen. The two-dimensional image on the display screen will include gray-scale representations of the internal organs and tissue masses of the anatomical site through which the cross-section was made. The second step is to select the interior of a ROI and draw a polygon within the boundaries of the cross-sectional view of this ROI. This polygon could also be drawn in the interior of a cancerous mass or other diseased tissue. The third step of the method of the present invention is to expand the polygon in a novel manner by iteratively testing pixels of the image on the display outside of, but adjacent to, the pixels that the polygon currently subtends. Pixels will be added to the polygon if the value of a decision rule function has a predetermined value. The expansion of the polygon is continued until none of the pixels at the perimeter of the polygon can satisfy the decision rule. Once it is found that none of the perimeter pixels satisfy the decision rule, the perimeter of the polygon is considered the boundary of the ROI. And the fourth step is that the boundary of the ROI is computed and a contour is developed based on this boundary. This same process is repeated for other ROIs that the user may select.

6 Claims, 7 Drawing Sheets

U.S. PATENT DOCUMENTS

| | | | |
|---|---|---|---|
| 5,319,549 | 6/1994 | Katsuragawa et al. | 364/413.13 |
| 5,319,551 | 6/1994 | Sekiguchi et al. | 382/131 |
| 5,410,617 | 4/1995 | Kidd et al. | 382/51 |
| 5,412,563 | 5/1995 | Cline et al. | 364/413.22 |
| 5,433,199 | 7/1995 | Cline et al. | 128/653.1 |
| 5,452,367 | 9/1995 | Bick et al. | 382/128 |
| 5,457,754 | 10/1995 | Han et al. | 382/128 |
| 5,458,126 | 10/1995 | Cline et al. | 128/653.1 |
| 5,491,627 | 2/1996 | Zhang et al. | 364/413.2 |
| 5,517,602 | 5/1996 | Natarajan | 395/119 |
| 5,531,223 | 7/1996 | Hatanaka | 128/653.2 |
| 5,537,485 | 7/1996 | Nishikawa et al. | 382/130 |
| 5,553,207 | 9/1996 | Sekihuchi et al. | 345/424 |
| 5,566,246 | 10/1996 | Rao | 382/154 |
| 5,570,430 | 10/1996 | Sheehan et al. | 382/128 |
| 5,574,799 | 11/1996 | Bankman et al. | 382/132 |
| 5,583,659 | 12/1996 | Lee et al. | 358/455 |
| 5,590,215 | 12/1996 | Allen | 382/128 |
| 5,669,382 | 9/1997 | Curwen et al. | 128/653.1 |

OTHER PUBLICATIONS

Fletcher et al., A Multispectral Analysis of Brain Tissues, *Magnetic Resonance in Medicine*, vol. 29, pp. 623–630 (1993).

Miller et al., Mathematical Textbook of Deformable Neuroanatomies, *Proceedings of the National Academy of Sciences USA*, vol. 90, pp. 11944–11948 (1993).

Staib et al., Boundary Finding with Parametrically Deformable Models, *IEEE Transactions on Pattern Analysis and Machine Intelligence*, vol. 14, pp. 859–870 (1996).

Chakraborty et al., Deformable Boundart Finding in Medical Images by Integrating Gradient and Region Information, *IEEE Transactions on Medical Imaging*, vol. 15, pp. 859–870 (1996).

McInerney et al., Deformable Models in Medical Image Analysis, *Proceedings of Mathematical Methods Biomedical Image Analysis*, pp. 171–180 (1996).

Giardina et al., Accuracy of Curve Approximation by Harmonically Related Vectors with Elliptical Loci, *Computer Graphics and Image Processing*, vol. 6, pp. 277–285 (1977).

Kuhl et al., Elliptic Fourier Features of a Closed Contour, *Computer Graphics and Image Processing*, vol. 18, pp. 236–258 (1982).

Wells et al., Adaptive Segmentation of MRI Data, *IEEE Transactions on Medical Imaging*, vol. 15, No. 4, pp. 429–442 (1996).

Cline et al.; Three–Dimensional Segmentation of MR Images of the Head using Probability and Connectivity; (1990); *Journal of Computer Assisted Tomography*, vol. 14(6): pp. 1037–1045, no month.

Cline et al.; 3D Reconstruction of the Brain from Magnetic Resonance Images using a Connectivity Algorithm; (1987); *Magnetic Resonance Imaging*, vol. 5: pp. 345–352, no month.

Cline et al.; Vascular Morphology by Three–Dimensional Magnetic Resonance Imaging; (1989); *Magnetic Resonance Imaging*, vol. 7: pp. 45–54, no month.

Bezdek et al.; Review of MR Image Segmentation Techniques using Pattern Recognition; (1993); *Medical Physics*, vol. 20(4): pp. 1033–1048, no month.

DeCarli et al.; Method for Quantification of Brain, Ventricular, and Subarachnoid CSF Volumes from MR Images; (1992); *Journal of Computer Assisted Tomography*, vol. 16(2): pp. 274–284, no month.

Höhne et al.; Interactive 3d Segmentation of MRI and CT Volumes using Morphological Operations; (1992); *Journal of Computer Assisted Tomography*, vol. 16(2): pp. 285–294, no month.

Kohn et al.; Analysis of Brain and Cerebrospinal Fluid Volumes with MR Imaging; (1991); *Radiology*, vol. 178: pp. 115–122, no month.

Neal et al.; Technical Note: Evaluation of a Region Growing Algorithm for Segmenting Pelvic Computed Tomography Images During Radiotherapy Planning; (1994): *The British Journal of Radiology*, vol. 67: pp. 392–395, no month.

Yin et al.; Comparison of Bilateral–Subtraction and Single––Image Processing Techniques in the Computerized Detection of Mammographic Masses; (1993); *Investigative Radiology*, vol. 28(6): pp. 473–481, no month.

Vaidyanathan et al.; Comparison of Supervised MRI Segmentation Methods for Tumor Volume Determination During Therapy: (1995); *Magnetic Resonance Imaging*, vol. 13(5): pp. 719–728, no month.

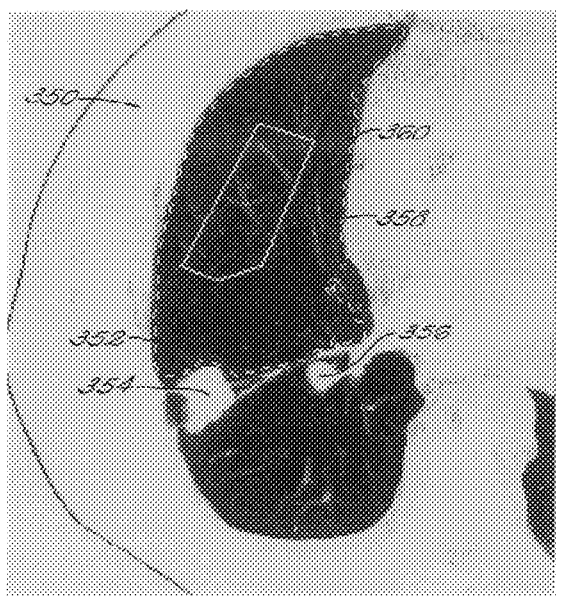
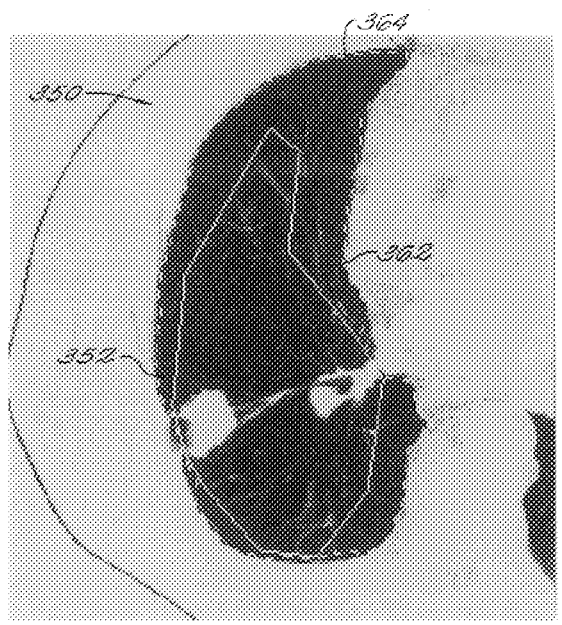
*FIG. 11*　　　　　　　　*FIG. 12*

AUTOSEGMENTATION/AUTOCONTOURING SYSTEM AND METHOD FOR USE WITH THREE-DIMENSIONAL RADIATION THERAPY TREATMENT PLANNING

FIELD OF THE INVENTION

The present invention relates to systems and methods that are used for three-dimensional radiation therapy treatment planning. More specifically, the present invention relates to systems and methods that are used for autosegmentation or autocontouring of images for three-dimensional radiation therapy treatment planning.

BACKGROUND OF THE INVENTION

When it is discovered that an individual has a disease, such as cancer, generally, there may be a mass of infected tissue that is desired to be observed to determine the extent of the disease and how any proposed treatment may affect the diseased tissue. Moreover, an individual may have some type of abnormality in an internal organ that also is desired to be observed in order to determine the proper type of treatment that is needed.

There now exists a number of systems that may be used to observe cancerous masses or abnormal organs. For example, X-ray, magnetic resonance imaging ("MRI"), computed tomography ("CT"), or other similar types of systems non-invasively provide the needed observations and produce an image of an area to be observed. If an X-ray (plane radiograph) is used, the two-dimensional image that is produced is a two-dimensional view of a projection of a three-dimensional volume of tissue. On the other hand, if MRI or CT systems are used, each two-dimensional image that is produced is a cross-sectional slice of a three-dimensional volume.

To view the infected tissue mass or abnormal organ, a series of two-dimensional images of sections of the patient can be combined to produce a three-dimensional image, or reconstruction, of the patient's internal anatomy. The two-dimensional images must be aligned, so that the most accurate correspondences between anatomic units are maintained. Digital images obtained directly from a CT or MRI scanner are automatically in register (provided no patient motion occurred during the scan), and may be used directly to create three-dimensional reconstructions. If the images are digitized from hard copy film records of a CT or MRI scans, the resulting digital images must be aligned to produce the needed correspondences. There exist several known methods for accomplishing this alignment, either by computational or interactive means.

A resulting three-dimensional reconstruction is a representation of the patient anatomy which contains abnormal tissue in a subset of the reconstruction. This subset may be referred to as volume of interest. This volume may be viewed in several ways. The simplest way is to view the original CT or MRI section images, or two-dimensional images which are derived from the original section images which present views of the volume of interest in planes that are orthogonal or oblique to the original section images. Alternatively, two-dimensional image data from multiple sections can be combined to form three-dimensional representations in which the anatomic units are depicted as solid opaque or translucent objects that may be interactively rotated, translated, and scaled using conventional computer graphics viewing program.

The three-dimensional reconstruction of the volume of interest containing diseased tissues or abnormal organs is created so that the spatial shapes, locations, and arrangements of organs may be used to prepare a three-dimensional radiation therapy treatment plan ("RTTP"). To develop the RTTP, the organ shape and arrangement information may be obtained from the three-dimensional reconstruction. Specifically, organ and tumor boundaries may be recorded from the two-dimensional images comprising the three-dimensional reconstruction. The two-dimensional images may be viewed on a computer graphics display and the edges of the organs and other relevant objects in the images may be recorded by manually tracing the edges in the displayed graphic using graphic control devices, typically a mouse and screen cursor combination. Resolution within the original two-dimensional section images is related to the pixel-to-pixel distance determined by the scanner settings, and the resolution in the third dimension is related to the section-to-section distance.

Three-dimensional reconstructions may be displayed in several formats. One such format is shown in FIG. 1A. FIG. 1A shows head surface 112, which is constructed from traverse CT sections. After points or areas of interest, or anatomical boundaries, are selected in two-dimensional images, a three-dimensional reconstruction containing these boundaries may be formed for the volume of interest containing the site or sites of disease. An example of cancerous mass 104 in the head 112 is shown in FIG. 1B. The radiation treatment plan objective is to irradiate the volume of diseased tissue with the appropriate dose and, as much as possible, not affect surrounding healthy tissues.

Additional three-dimensional reconstructions of the cancerous mass created from CT or MRI scan during or after radiation therapy, can indicate whether the treatment is having the desired effect of reducing the size of the cancerous mass. Moreover, the additional three-dimensional reconstruction of the cancerous mass at its location on or in an organ also may be used to determine whether surgical techniques have been successful in removing the cancerous mass. If it has not been totally removed, the three-dimensional reconstruction will show what remains so that further treatment may be planned.

A RTTP is a collection of data that is used to calculate radiation dosages for a cancerous mass. RTTP includes anatomical data about the patient being treated and defines the volume, area, or point where radiation doses are to be calculated.

The anatomical data about the patient being treated may be derived from pixel images and contours. Pixel images, in this context, are data files corresponding to CT or MRI images that contain an array of numeric values which represent the image intensifies of the patient in a defined plane, i.e., transverse, sagittal, or coronal. These values may be used to reconstruct the image for display on a computer display. A pixel image is shown in FIG. 2, generally at 150.

Contours are connected line segments which define the outlines of individual anatomic or structural elements in a particular plane. These elements may include a patient outline, diseased tissue outline, and individual organ outlines, to name a few. A set of contours is shown in FIG. 3, generally at 175. Contours may be created using a manual digitizer to trace drawings from graph paper, a radiograph, or a hard copy of a CT or MRI image. Contours also may be created using a graphics control device such as a mouse to either trace a pixel image directly from a screen display or to define an area of the image for autocontouring.

Contours created by either of the methods just described are cross-sections of the boundaries of the anatomic units that may be used to create a three-dimensional reconstruction of the volume of interest displaying the spatial relationships among the anatomic units. It is necessary to make a series of these cross-sections that extend the length of the cancerous mass or target area, so that the entire tumor and all relevant neighboring anatomic units may be displayed.

The set of cross-sections associated with the cancerous mass or target volume may be referred to as data pools. Data pools may be further divided into study sets. The study sets are sets of cross-sections or information from specific cross-sections that are intended to be used with respect to a specific RTTP. A study set may be an entire data pool or just some elements of a data pool. The relationship between data pools and study sets is shown in FIG. 4, generally at 200.

Referring to FIG. 4, data pool 202 includes ten cross-sections. Shown below data pool 202 are three study sets. These are Study Set A 204, Study Set B 206, and Study Set C 208. Both Study Set A 204 and Study Set B 206 include cross-sections that are part of data pool 202. On the other hand, Study Set C 208 includes the entire data pool.

In the production of the cross-sections for the data pools and study sets, the body section of interest, such as head, neck, or prostate, define an anatomical site and the internal structures or areas of interest for which contours are constructed are anatomical structures. Anatomical structures include the heart, lungs (left and right), and the spinal cord, etc.

The calculation region is the region in the patient's anatomy where the radiation dose will be calculated under the RTTP, and is a subset of the volume of interest in the three-dimensional reconstruction. All of the points located in the region are used during dose calculation. Referring to FIG. 5, generally at 225, calculation volume 226 is indicated for head 228. The calculations will be made for volume 226. Conventional methods are used for making the actual dose calculations which will be applied in carrying out the RTTP.

Before the RTTP can be computed, the spatial locations and distributions of the diseased tissues and the neighboring normal anatomic structures must be defined using the traced contours. The treatment plan is designed so that the tumor and a surrounding volume are maximally and evenly irradiated while restricting, as much as possible, irradiation of neighboring sensitive tissues most likely to be damaged by radiation.

The development of accurate contours for the cross-sections of anatomic structures and diseased tissues is the most time-consuming aspect of the preparation of a RTTP. In most cases, the three-dimensional reconstruction is formed from a multi-planar CT or MRI study. Generally, the contours for each of the areas of interest must be traced from CT or MRI hard copy images or digital CT or MRI slice images. The contours that result define the volumes and shapes of the organs and diseased masses in the volume of interest. The time to perform this labor intensive task increases sharply with an increase in resolution corresponding to an increased number of cross-sections used to form the three-dimensional reconstruction. Contour preparation typically may take two to three hours and in some cases substantially more than this amount of time.

Segmentation is the subdividing of an image into discrete regions. In the present situation, it is subdividing an image into the anatomical units required to prepare a RTTP. Since an object can be equivalently described by its boundary or a map of its regional extent in the image, contouring, and segmentation may be complementary operations.

A number of autosegmentation methods have been proposed, and they can be divided into two main types: global and local. The global type seeks to contour all the organs/tumors/anatomical units in a CT or MRI image simultaneously in one computational operation. Such methods frequently use neural networks to implement clustering algorithms on the statistical feature space of an image. Two reviews of global segmentation methods in CT/MRI imaging are: Bezdek, J. C., Hall L. O., and Clarke L. P., "Review of MR image segmentation techniques using pattern recognition," *Medical Physics,* 20:1033–1048, 1993, and Vaidyanathan, M., Clarke, L. P., Velthuizen, R. P., et al., "Comparison of supervised MRI segmentation methods for tumor volume determination during therapy," *Magnetic Resonance Imaging,* 13:719–728, 1995. Applications of neural networks implementing fuzzy clustering algorithms in such applications has been reported in the following document: Bezdek, J. C. and Pal, S. K., *Fuzzy Models for Pattern Recognition,* IEEE Press, Piscataway, N.J., 1992. What is gleaned from these articles is that there is not a method that is capable of accurate segmentation of many image types. This is because different organs in many cases have similar gray-scale level property distributions, and high variances of these properties within organs. These particular problems pose very significant difficulties, and have prevented the wider use of automated image segmentation in medical imaging.

Now turning to the local type, local autosegmentation seeks to contour organs or lesions singly, based on some user-input information. Systems have been reported which purport to accurately segment the brain from the CT or MRI scans of the head. An example is reported in Cline, H. E., Lorensen, W. E., Kikinis, R., and Jolesz, F., "Three-dimensional segmentation of MR images of the head using probability and connectivity," *Journal of Computer Assisted Tomography,* 14:1037–1045, 1990. However, no local type has been reported that works successfully on a range of tissues from many different parts of the body.

It would be highly desirable to have an autosegmentation/autocontouring method that would significantly reduce the amount of time to accomplish accurate segmentation and not have the problems of prior autosegmentation/autocontouring systems and methods.

SUMMARY OF THE INVENTION

The present invention is an autosegmentation/autocontouring method that quickly and accurately defines the boundaries around regions in two-dimensional images for the development of cross-sections that may be incorporated into a three-dimensional reconstruction of a patient volume of interest. The method of the present invention substantially reduces the time it takes to create a contour to less that 5 seconds (sec.) per cross-section.

The autosegmentation/autocontouring method of the present invention includes at least four steps. In the first step, the user, with the assistance of a computer, digitizes a CT image and displays it on a display screen. The two-dimensional image on the display screen will include gray-scale representations of the internal organs and tissue masses of the anatomical site through which the cross-section is taken.

The second step is to sample the interior of a region of interest ("ROI"), an anatomical unit for which autosegmentation/autocontouring is to be performed. If the volume of interest is the torso, the ROI could be the right lung. To sample the ROI, the user will draw a polygon entirely within the boundaries of the cross-sectional view of the ROI as it appears on the display screen. This sample polygon also could be drawn in the interior of a cancerous mass or other visually distinct diseased tissue. The only requirement in drawing the polygon is that it not extend past any of the apparent boundaries of the ROI.

The third step of the method of the present invention is to expand the polygon in a novel manner by iteratively testing pixels of the image outside of, but adjacent to, the pixels that currently belong to the polygon. The testing procedure will result in a pixel being added to the polygon if the value of a decision rule exceeds a predetermined value. To do this, a decision rule encodes information about both the pixels inside and outside of the polygon. The expansion of the polygon is based on individual elements, e.g., spinal cord, left lung, right lung, heart, etc., having pixel gray-scale level properties different than those of adjacent structures and gray-scale level properties that are statistically constant across the ROI. The polygon is expanded until none of the pixels at the perimeter of the polygon can satisfy the decision rule.

The fourth step of the method is the calculation of the perimeter or boundary of the ROI from the polygon in its latest, updated state.

An object of the present invention is to provide a method for autosegmentation/autocontouring that significantly reduces the time necessary to develop contours, and hence RTTPs.

Another object of the present invention is to provide a method for autosegmentation/autocontouring that in part uses an algorithm that controls the expansion of the polygon until the polygon subtends this entire area of a region of interest.

A further object of the invention is to provide a method for autosegmentation/autocontouring that expands a polygon drawn in an region of interest based on the individual elements, e.g., spinal cord, left lung, right lung, heart, etc., having pixel gray-scale level properties different than those of all adjacent structure and such properties are statistically constant across a region of interest.

BRIEF DESCRIPTION OF THE DRAWINGS

FIG. 11 shows a CT slice in which the initial polygon expanded to a contour that did not match an apparent anatomical boundary of an object.

FIG. 12 shows the CT slice in FIG. 11 with a initial polygon that resampled the object so that the initial polygon will expand to match the apparent anatomical boundary of the object.

DETAILED DESCRIPTION OF THE INVENTION

Figure 1A:
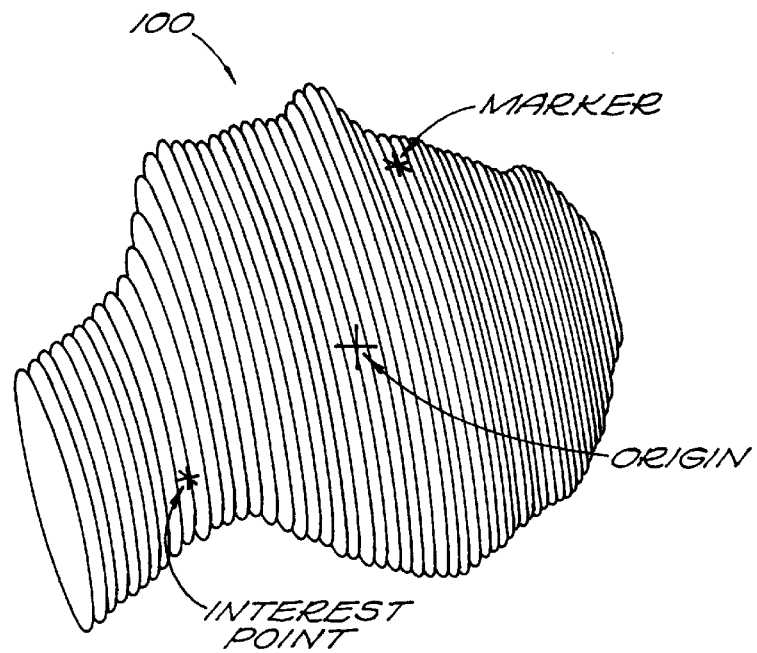
FIG. 1A is a perspective view of a three-dimensional image that is formed from a plurality of aligned cross-sections that have been contoured to represent the exterior of the head.
Figure 1B:
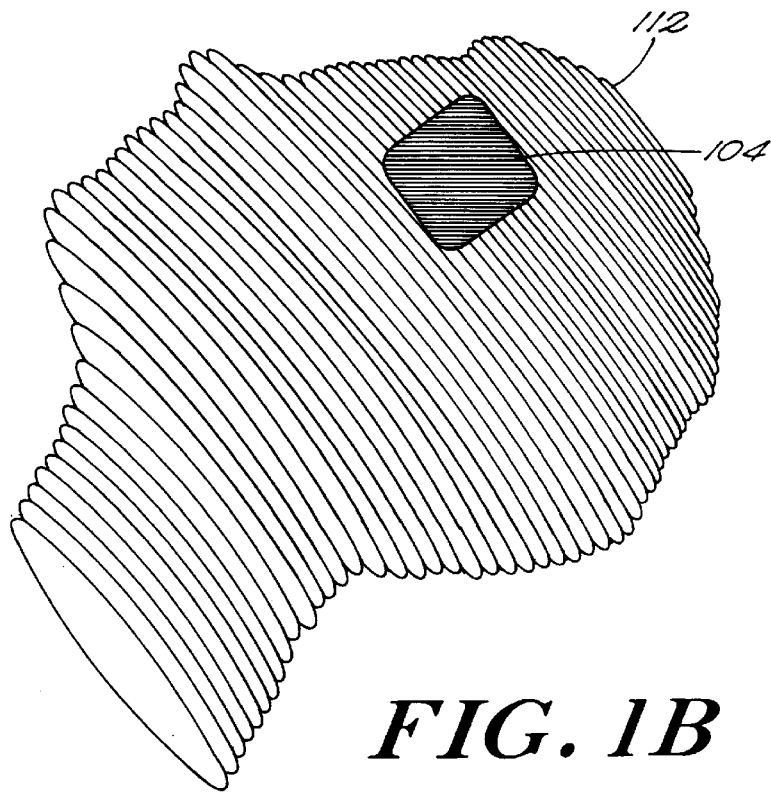
FIG. 1B is a perspective view of a three-dimensional image that is formed from a plurality of aligned cross-sections that have been contoured to represent the exterior of the head and a cancerous mass in the head.
Figure 2:
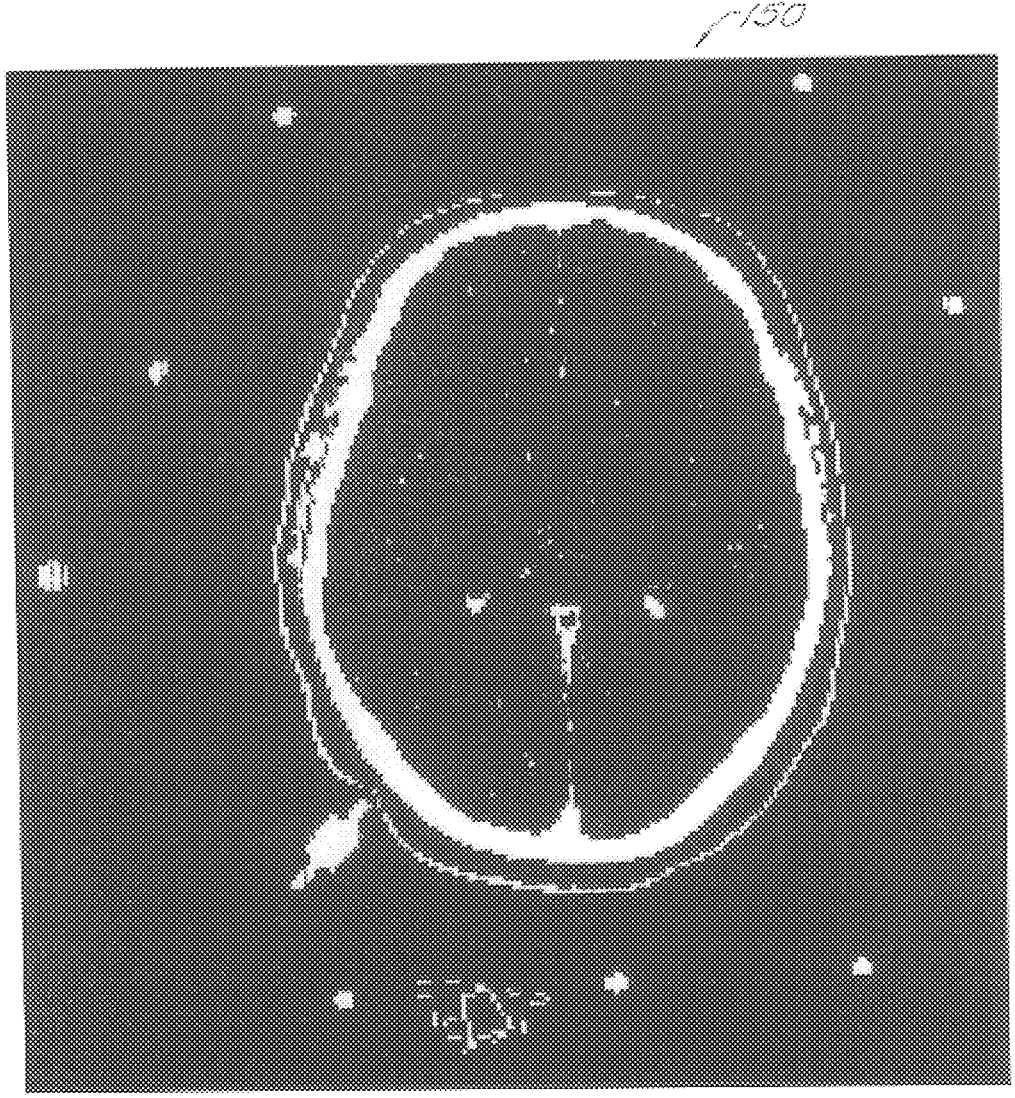
FIG. 2 is sample pixel image that may be used for developing contours.
Figure 3:
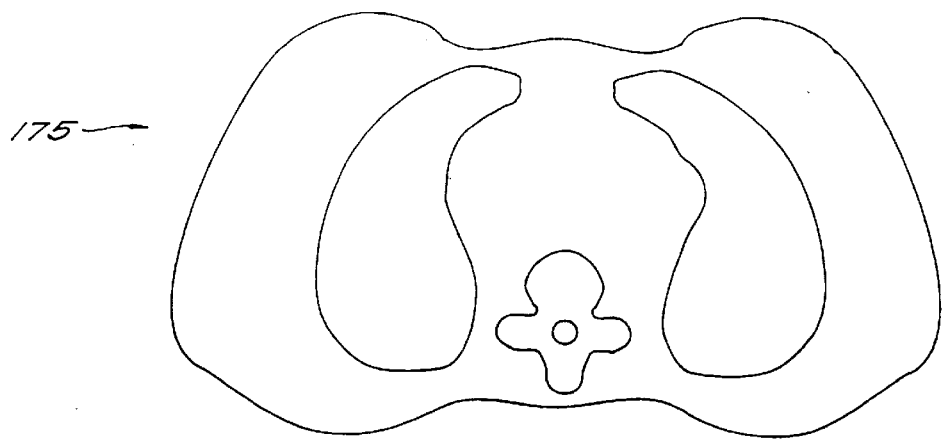
FIG. 3 is a sample contour that was created by tracing, for example, a CT image.
Figure 4:
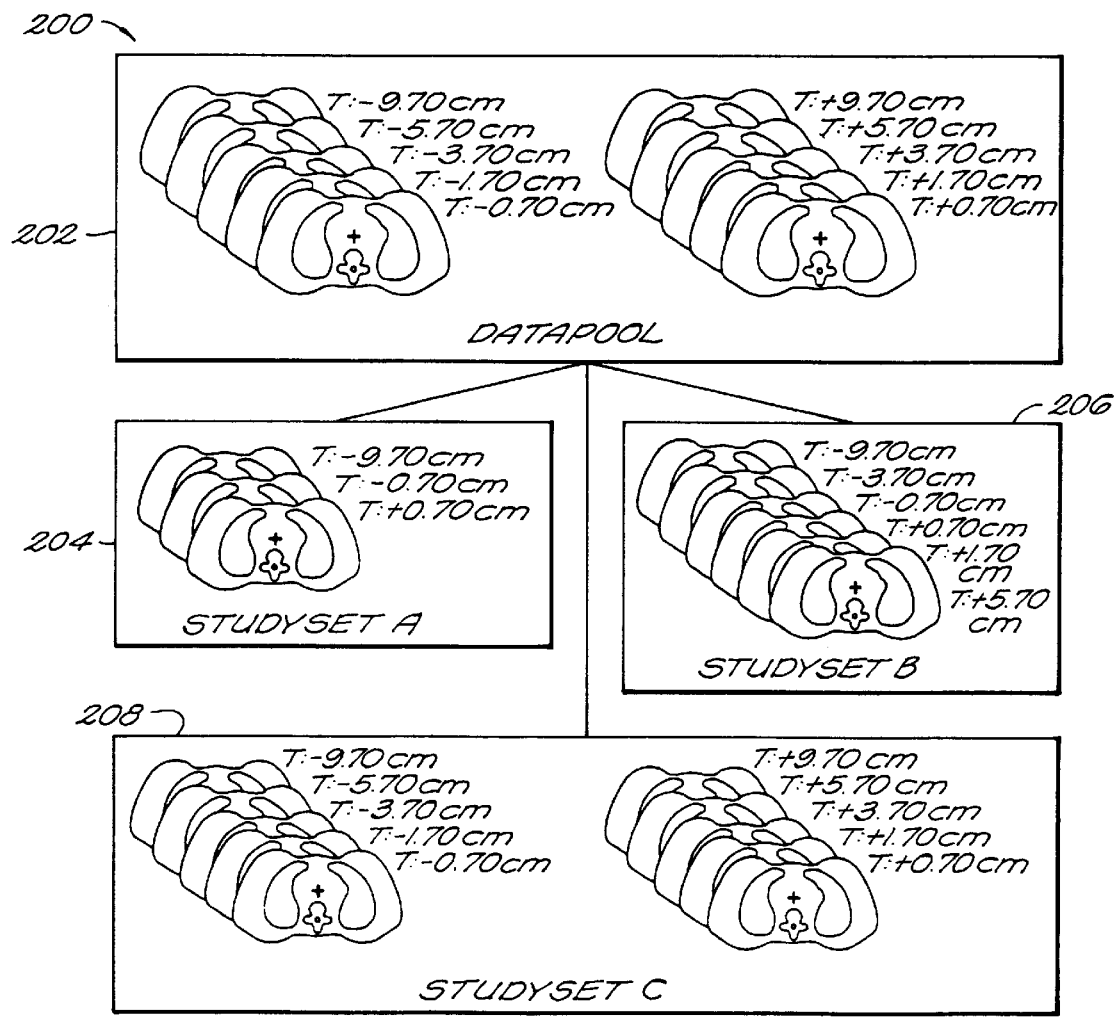
FIG. 4 shows the relationship between data pools and study sets that are used in radiation therapy treatment planning.
Figure 5:
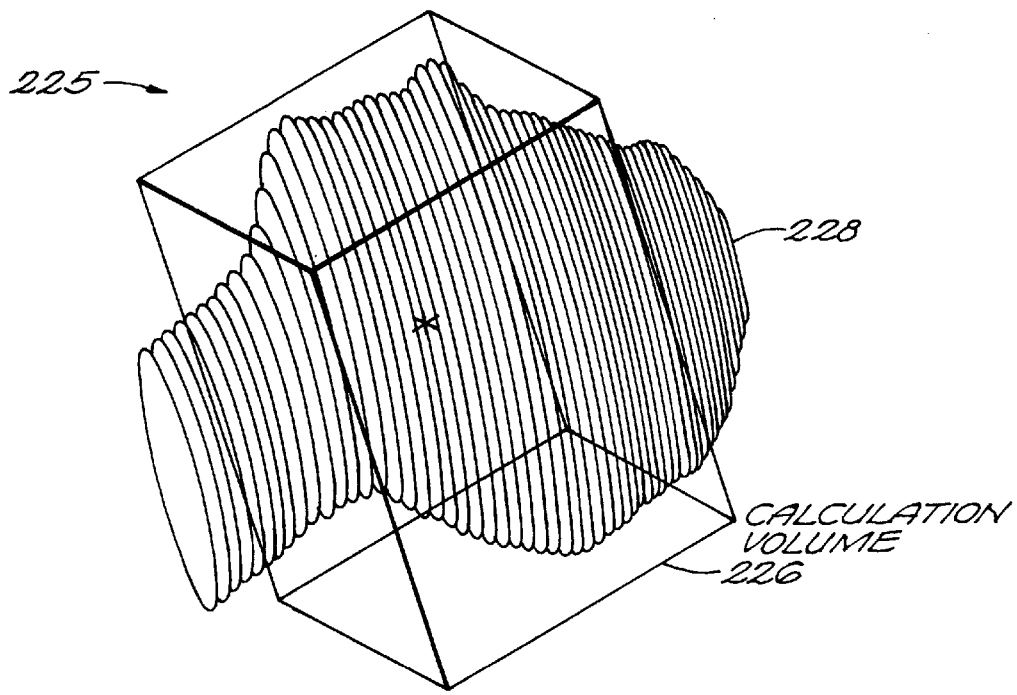
FIG. 5 is a perspective view of a three-dimensional image that is formed from a plurality of aligned cross-sections that have been contoured to represent the exterior of the head and a calculation volume also is shown.

The present invention is an autosegmentation/autocontouring method that quickly and accurately defines boundaries around regions for the development of cross-sections that may be aligned to form a three-dimensional reconstruction of a patient's anatomy.

The autosegmentation/autocontouring method of the present invention includes at least four steps. After a brief discussion of these four steps, the method of the present invention will be discussed in greater detail.

The first step is to digitize a CT, MRI, or other suitable image, and display it on a display screen. The two-dimensional image on the display screen will include gray-scale representations of the internal organs and tissue masses of the anatomical site through which the cross-section is taken.

The second step is to sample the interior of a ROI by drawing a polygon entirely within the boundaries of the cross-sectional view of this ROI. The ROI may correspond to any anatomic unit (organ, tumor) whose representation is to be included in the three-dimensional reconstruction of the patient volume of interest.

The third step of the method of the present invention is to expand the polygon in a novel manner by iteratively testing pixels of the image on the display outside of, but adjacent to, the pixels that currently belongs to the polygon. Pixels will be added to the polygon if the value of a decision rule exceeds a predetermined threshold. The expansion of the polygon is continued until none of the pixels at the perimeter of the polygon can satisfy the decision rule.

According to the fourth step, the boundary of the ROI is computed from the polygon in its latest, updated state. This same process is repeated for other ROIs that the user may select.

The first and second steps of the method of the present invention require the user to perform specific tasks. These are the selection of the ROI and the drawing of a polygon within the apparent boundaries of the ROI. The next step, Step 3, governs the expansion of the polygon to the boundaries of the ROI even if the boundary, as it appears, is not complete and continuous.

The expansion of the polygon to adjacent pixels may be based on minimum Bayes risk analysis which provides, on average, that the results of classification decisions will have the lowest overall risk of loss due to error. This expansion also may be based on minimum Bayes error analysis (minimum-risk analysis with a zero-one loss function) which guarantees that classification decisions, on average, will have the lowest possible error. Either rule classifies the pixels outside of the polygon to determine if they should be added to the polygon. The decision rule operates on a set of gray-scale level properties computed for all of the pixels in two classes: those inside of the polygon and those outside of the polygon. A statistically complete description of each property in each class is given by the property's probability density function which can be depicted graphically by a histogram. These properties will be used to form discriminant functions used by a decision rule to classify pixels as belonging inside or outside the ROI.

In the preferred embodiment of the present invention, a minimum Bayes error decision rule is used to control the expansion; however, it is understood that the Bayes risk analysis using suitable loss functions also may be used to control the expansion. Reviews of Bayesian decision making in statistical pattern recognition is reported in the following sources: Van Trees, H. L., *Detection, Estimation and Modulation Theory, Part I,* Wiley, New York, 1968, Duda, R. O., and Hart, P. R., *Pattern Classification and Scene Analysis,* Wiley, New York, 1973, and Fukunaga, K., *Introduction to Statistical Pattern Recognition, 2nd Ed.,* Academic Press, New York, 1990.

The minimum Bayes error decision rules, as they apply to the autosegmentation/autocontouring method of the present invention, are based on a number of expressions and presumptions. These expressions and presumptions will now be discussed.

X represents a vector whose component values are the values of the gray-scale level-derived properties for a single pixel that is being tested for inclusion with the polygon. The components of vector X will be discussed in detail subsequently.

The gray-scale level derived properties usually have different distribution of values in different classes. This information exists in class conditional probability density functions represented by P(X|i), which is the probability of observing the vector X gray-scale level-derived properties given class i. Here i is a class label and can represent inside and outside pixels. Further, the probability that class i is observed, relative to all the classes present, is the a priori probability P(i). The probability that class i is the correct class given vector X is the a posteriori probability P(i|X), which is related to the other two probabilities by Bayes rule given by Expression (1):

$$P(i|X) = \frac{p(X|i)P(i)}{\sum_j p(X|j)P(j)} \qquad (1)$$

where, p(X|i)=The probability of observing vector X given class i.

p(X|j)=The probability of observing vector X given class j.

P(i|X)=The a posteriori probability of observing class i given vector X.

$\Sigma_j p(X|j)P(j)$=The sum of the products of the probability of observing vector X given any class j and the a priori probability of class j, for all j classes.

P(i)=The a priori probability that class i is observed.
P(j)=The a priori probability that class j is observed.

Given Expression (1), the decision rule for two classes, for example, classes i and j, where i could represent the class of pixels inside the polygon and j could represent the pixels outside the polygon, is to choose that class associated with the largest a posteriori probability. This rule is represented by Expression (2):

if $P(i|X) > P(j|X)$, decide class i, else decide class j  (2)

where,

P(i|X)=The a posteriori probability of observing class i given vector X.

P(j|X)=The a posteriori probability of observing class j given vector X

If more than two classes are present, then the class with the maximum a posteriori probability is chosen according to Expression (3):

if $i = \arg\max_j [P(j|X)]$, decide class $i$  (3)

where, $$\arg\max_j [P(j|X)]$$

=The value of the class label j corresponding to the largest a posteriori probability P(j|X).

As stated, Expression (3) is the maximum a posteriori probability rule. If prior probabilities are equal, then the class conditional probabilities may be combined in a likelihood ratio test as set forth in Expression (4):

if $\frac{p(X|i)}{p(X|j)} > 1$, decide class i, else decide class j  (4)

where, p(X|i)=The probability of observing vector X given class i.

p(X|j)=The probability of observing vector X given class j.

If, however, the prior probabilities are not equal, as would apply in the present invention, then the maximum a posteriori probability rule for the classes, as set forth in Expression (2), is the correct rule to use.

Expression (2), when examined, can be written in a more convenient form for use in the method of the present invention. In viewing Expression (2) in this manner, it is to be understood that the $P(i|X) \propto p(X|i)P(i)$ because the denominator in Expression (1) is a constant, so Expression (2) may be written as set forth in Expression (5):

$p(X|i)P(i) > p(X|j)P(j)$, decide class i, else decide class j  (5)

where, p(X|i)=The probability of observing vector X given class i.

P(i)=The a priori probability that class i is observed.

p(X|j)=The probability of observing vector X given class j.

P(i)=The a priori probability that class j is observed.

For reasons of computational convenience, discriminant functions, represented by $g_i(\ )$, of the product of p(X|i)P(i) are often used. If the $g_i(\ )$s are monotonically increasing, they may be substituted in Expression (5) without changing the fundamental nature of the decision rule. Thus, a pixel with vector X is assigned to class i according to Expression (6):

$g_i(X) > g_j(X)$, decide class i, else decide class j  (6)

where, $g_i(X)$ = A function of the a posteriori probability $P(i|X)$.
$g_j(X)$ = A function of the a posteriori probability $P(j|X)$.
One such appropriate monotomically increasing function is shown in Expression (7):

$$g_i(X) = \log p(X|i) + \log P(i) \qquad (7)$$

where, log $p(X|i)$ = The logarithm of the conditional probability of vector X given class i.

log $P(i)$ = The logarithm of the a priori probability of class i.

There may be some difficulty using Expressions (5) or (6) directly as decision rules because evaluating the conditional probability densities $p(X|i)$, $p(X|j)$ requires the resampling of histograms of measured, and often sparse, data into sets of discrete intervals. A more convenient and less computationally complex approach is to model the data vector X as a parameterized function of the densities and use the parameters to perform the inter-class comparisons. According to the method of the present invention, the gray-scale level-derived features of a pixel are modeled as a multivariate Gaussian distribution that has a class conditional probability density according to Expression (8):

$$p(X|i) = \left[ \frac{1}{2\pi^{\frac{d}{2}} |\Sigma_i|^{\frac{1}{2}}} \right] \exp\left[ -\left(\frac{1}{2}\right)(X-M_i)^T \Sigma_i^{-1} (X-M_i) \right] \qquad (8)$$

where, d = The number of feature-components in vector X.
$M_i$ = The vector of feature means for class i.
$\Sigma_i$ = The matrix of covariances for the features in class i.
$\Sigma_i^{-1}$ = The inverse covariance matrix for the features in class i.
T = Transpose of the resulting vector.

The i-th class mean vector components are the means, or expected values, of the data vector X, individual components $M_i = E[X]$, and the covariance matrix is expressed as shown in Expression (9).

$$\Sigma = E[(X-M_i)(X-M_i)^T] \qquad (9)$$

where,

E[ ] = Is the expected or average value of the quantity in the [ ].
X = vector X.
$M_i$ = The vector for the mean property.
T = Transpose of the resulting vector.

Substituting Expression (8) in Expression (6) with an understanding of Expression (9), and taking the logarithm of the density provides the determinant function in Expression (10):

$$g_i(X) = -\left(\frac{1}{2}\right)(X-M_i)^T \Sigma_i^{-1} (X-M_i) - \left(\frac{d}{2}\right)\log(2\pi) - \left(\frac{1}{2}\right)\log|\Sigma_i| + \log(P_i) \qquad (10)$$

where,

X = Vector X.
$M_i$ = The vector for the mean property.
$\Sigma_i$ = The matrix of covariances for the features in class i.
$\Sigma_i^{-1}$ = The inverse matrix of matrix $\Sigma_i$.
$|\Sigma_i|$ = The determinant of the covariance matrix.
T = Transpose of the resulting vector.
d = The number of feature-components in vector X.
P(i) = The a priori probability that class i is observed.

Given Expression (10), the maximum a posteriori probability test for the two classes, as is done in at least one embodiment according to the method of the present invention, is the decision whether to assign a given pixel to the class of pixels belonging to the sample polygon, such as class i, or to the class of pixels outside the sample polygon, such as class j, is given by previously provided Expression (6), which for convenience is expressed here:

$$\text{if } g_i(X) > g_j(X) \text{ decide class i, else decide j} \qquad (6)$$

where, $g_i(X)$ = class i discriminant function.
$g_j(X)$ = class j discriminant function.

The (d/2) log ($2\pi$) term which is constant for all classes and contributes no class-specific information is deleted in the form of $g_i(X)$ used in the preferred embodiment of the present invention.

The ROI boundary is computed from the locations of the pixels in the outermost layer of the fully-expanded sample polygon. The outermost layer of pixels in the sample polygon does not exactly coincide with the visually-apparent ROI boundary, but is consistently inside the ROI boundary. The reason is that the 3×3 pixel window on which the classifier features are calculated prevents the classifiers from identifying pixels in the ROI interior that are within one to two pixels from the actual edge. ROI edges correspond to abrupt changes in the gray-scale properties, and these pixels' properties consistently do not sufficiently resemble their ROI-interior neighbors' properties. The ROI edges are assumed to be steps in gray-scale value so that pixels classified as ROI-interior pixels, on average, could be no closer than two pixels from the actual edge. Therefore, the ROI boundary is taken as the sample polygon boundary expanded by two cycles of conversion of all polygon-adjacent, outside pixels to inside pixels.

The method of the present invention makes two presumptions regarding the anatomical objects in CT or MRI images. The first presumption is that discrete structures in CT or MRI images are statistically homogeneous. This means that discrete objects have substantially constant values for the mean and variance of gray-scale level-derived properties across the full extent of the structure. As such, the discrete structure's gray-scale level-derived proprieties may be described by a set of parameter constants that are useful in evaluating the probability decision rules. The likely result, if the first presumption is not met, is that the computed contour will not expand enough to fully match the discrete structure's apparent boundary.

The second presumption is that image objects are completely surrounded by a boundary in which the values of the gray-scale level-derived property statistics change significantly relative to constant values inside the ROI. If the second presumption is not met, the perimeter of the expanding polygon may extend beyond the boundary of the ROI into surrounding tissue.

The method of expanding the polygon to the boundary of the ROI is controlled by at least three specific features.

These features ensure that the polygon does not extend to the surrounding tissue.

The first feature is that the initial polygon is drawn so that it is entirely within the discrete structure (or object) to be contoured. If this not the case and the initial polygon extends over the boundary, the method of the present invention will not expand the initial polygon.

The second feature is that the polygon will only expand by attracting pixels that are outside pixels. This also is controlled by the fact that once a pixel is an inside pixel, it cannot be change or reverted to an outside pixel during the entire expansion.

The third feature is that any outside pixel that becomes completely surrounded by inside pixels is converted to an inside pixel. Thus, the perimeter of the polygon at full expansion will define a simply connected region with a closed boundary and which has no holes.

The vector $X=\{x_1 \ldots, x_n\}$ contains n components, each of which corresponds to a numeric value of a gray-scale level-derived property for a pixel. These values are computed on the set of pixels continued in the 3×3 pixel neighborhood centered on each given pixel. Such numeric values include the mean, standard deviation, skewness, kurtosis, energy, entropy, and the range. This is reported, for example, in Pratt, W. K., *Digital Image Processing, 2nd Ed.*, Wiley, New York, 1991, and Jain, A. K., *Fundamentals of Digital Image Processing*, Prentice Hall, New York, 1989. However, it is understood that there can be more gray-scale level-derived properties for which numeric values may be generated.

Figure 6:
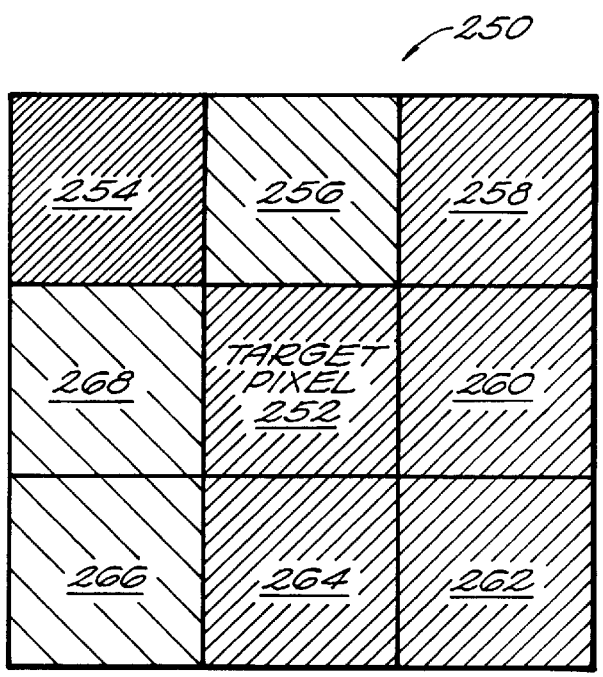
FIG. 6 is a graphical representation of a target pixel and the 3×3 set of pixels that influence the properties of the target pixel.

The area around each pixel is preferably defined by a 3×3 pixel set. This is shown graphically in FIG. 6, generally at 250. In FIG. 6, the pixel of interest is center pixel 252. The pixels that influence the numeric values of center pixel 252 are the 8 pixels adjacent to it. These are pixels 254, 256, 258, 260, 262, 264, 266, and 268. These 8 pixels and the center pixel form the 3×3 pixel set except for pixels at, or adjacent to, the polygon, as described below.

The values of the components $\{x_1 \ldots, x_n\}$ of the vector X are used to compute the mean property vector $M_i$ and the inverse covariance matrix $\Sigma_i^{-1}$ for each i-th class to generate the discriminant functions $g_i(\ )$ for each of the two classes used in the present invention. The functions $g_i(\ )$ are used to evaluate the decision rule specifically given in Express (6). The numerical values of the components $x_k$ of the vector X are computed from the gray-scale level intensity values of the pixels comprising the 3×3 neighborhood centered on the given pixel. For those pixels at, or adjacent to, the sample polygon border, neighborhood pixels in the opposite class are excluded from the calculation of the individual $x_k$. The resulting decision rule (Expression (6)) is called a supervised classifier denoting its use of data from known classes to construct the discriminant functions.

Given the foregoing, the method of the present invention will be discussed as the user would implement the method. The method that will be described making reference to the FIGS. 7–12.

Figure 7:
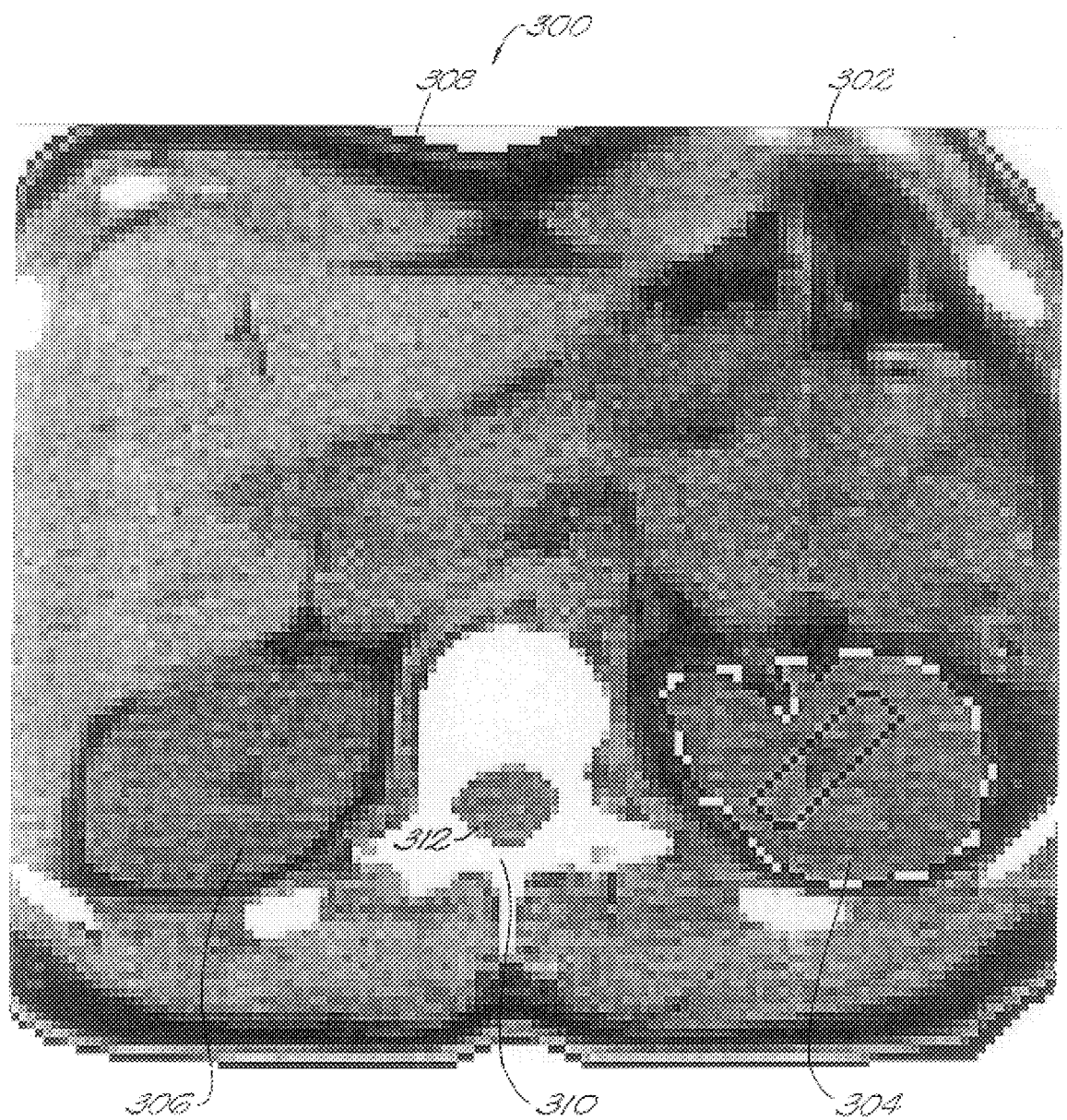
FIG. 7 shows a CT slice with an object that has an initial polygon and resulting contour shown.

FIG. 7, generally at 300, shows a CT section or slice that would be displayed on a display screen. In FIG. 7, CT slice 302, through the torso, shows the cross-sectional view of organs that are present. For example, CT slice 302 shows left kidney 304, right kidney 306, abdomen 308, vertebrae 310, and spinal cord 312. With regard to the CT slice that is shown on the display screen, a cursor/mouse button (not shown) is used to describe a simple polygon inside the structure to be contoured. In FIG. 7, simple polygon 314 is shown drawn in kidney 304. The polygon is expanded according the decision rules discussed previously. In this Figure, black and white dashed line 316, which is the computed contour for kidney 304, is the result of the expansion of polygon 314 according to the decision rules of the method of the present invention.

Figure 8:
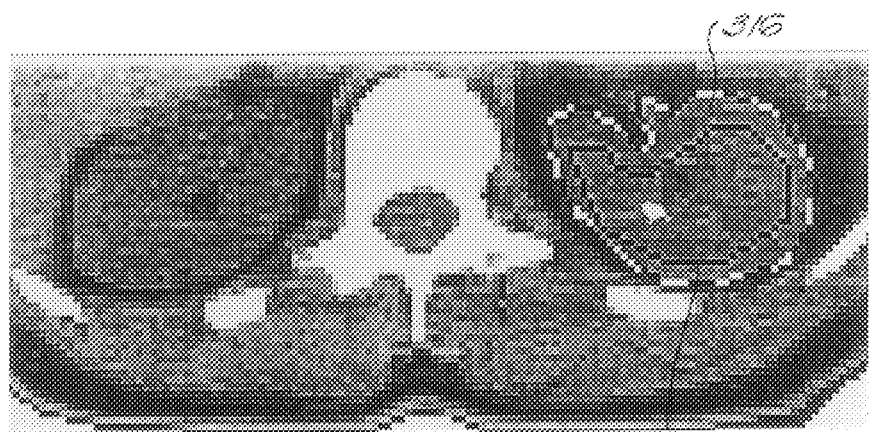
FIG. 8 shows the CT slice in FIG. 7 with a differently shaped initial polygon that results in substantially the same contour as shown in FIG. 7.
Figure 9:
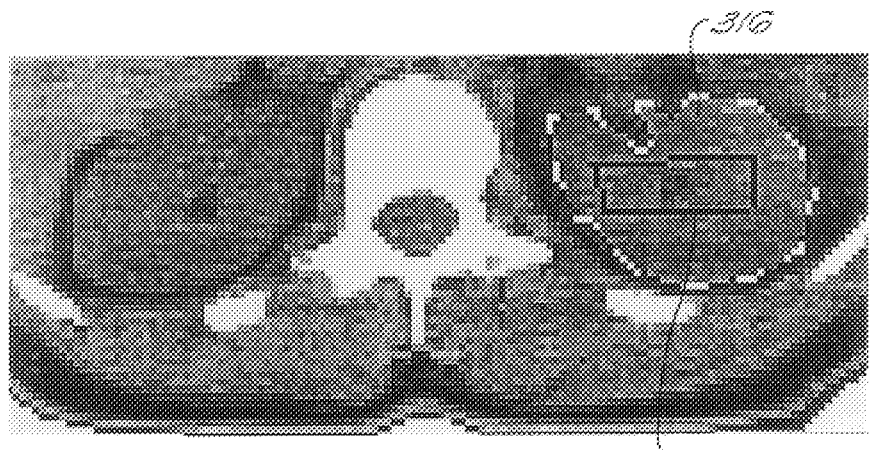
FIG. 9 shows the CT slice in FIG. 7 with a differently shaped initial polygon that results in substantially the same contour as shown in FIG. 7.
Figure 10:
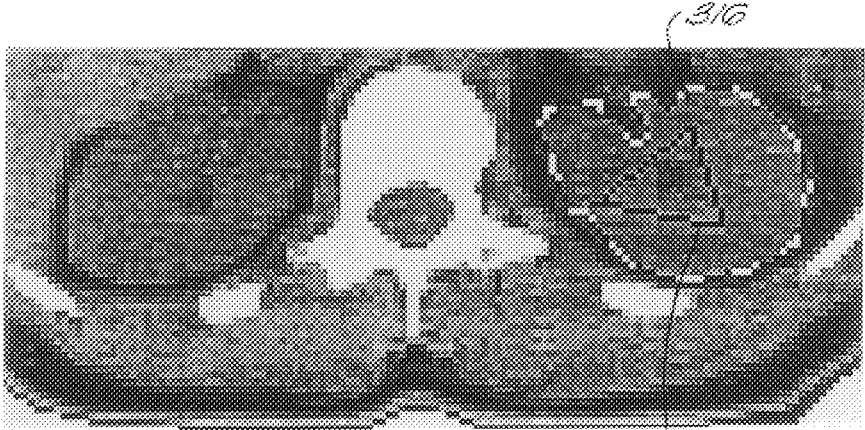
FIG. 10 shows the CT slice in FIG. 7 with a differently shaped initial polygon that results in substantially the same contour as shown in FIG. 7.

It is to be understood that the initial, sample polygon may be any shape as long as it is formed within the ROI, and has an area greater than a threshold minimum area. In FIGS. 8, 9, and 10, show different initial polygons that result in the same contour, contour 316. Specifically, in FIG. 8, initial polygon 318 expands to contour 316; in FIG. 9, initial polygon 320 expands to contour 316; and in FIG. 10, initial polygon 322 expands to contour 316.

In situations where the computed contour does not visually match the apparent anatomical boundary, the user may resample the particular ROI so a better match will obtain. The resampling concept will be illustrated by referring to FIGS. 11 and 12.

Referring to FIG. 11, a portion of slice 350 is shown. In this portion, the cross-section of right lung 352 is shown. As shown, right lung 352 has abnormal mass 354 opposite main bronchus 356. In FIG. 11, polygon 358 was drawn in the anterior lung. When polygon 358 was expanded, contour 360 was computed. In expanding polygon 358, contour 360 covered only the anterior lung and did not cross the mass/bronchus features. It is readily seen that there is not a match between contour 360 and the apparent anatomical boundary of the right lung. This is the type of situation requiring resampling to obtain an accurate contour.

Referring to FIG. 12, left lung 352 has polygon 362 drawn in it. The new polygon is drawn in the anterior and posterior portions of right lung 352. When polygon 362 is expanded according to the method of the present invention, contour 364 is formed that substantially matches the apparent anatomical boundary of right lung 352.

Resampling also may be necessary if certain other conditions arise. For example, if the object for which a contour is to be computed is statistically inhomogeneous, resampling may be necessary. In such a situation, the computed contour may not accurately fill the ROI. Here, the user should redraw the initial polygon to sample that portion of the object that was not included (in a fashion similar to what was done in FIG. 12). Another situation when resampling is needed, when the object is not completely surrounded by a significant boundary. In this case, the contour that is formed may extend to tissue outside of the object. To obtain an accurate contour, the user should edit the computed boundary by removing the incorrect boundary segment and provide a boundary segment in the proper place.

The described method has been for a single slice. However, it is understood that the autosegmentation/autocontouring method of the present invention include simultaneously contouring an object on a plurality of slices. Moreover, it is understood that multiple objects may be contoured simultaneously and on a plurality of slices.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

I claim:

1. An autocontouring method, comprising the steps of:
   (a) producing a two-dimensional image of a structure with the structure having at least one object disposed therein and the object is substantially defined by boundary, with an area within the boundary being of a first class of material and an area outside of the boundary being of a second class of material;

(b) forming a polygon in the object such that the polygon is fully within the boundary of the object and the polygon subtends only a first class of material;

(c) testing a discrete portion of an area outside of, but adjacent to, the polygon according to a maximum a posteriori decision rule according to an Expression if $g_i(X) > g_j(X)$, decide the first class of material, else decide the second class of material, where, $g_i(X)$=discriminant function for a class of material, denoted i;

$g_j(X)$=discriminant function for a class of material, denoted j;

(d) expanding the polygon to include the discrete portion tested at step (c) if it is determined that the discrete portion is of a first class of material;

(e) repeating steps (c) and (d) until the testing at step (c) determines that at each location outside of, and adjacent to, a polygon expanded according to steps (c) and (d), a discrete portion tested at step (c) is of second material; and (f) computing a boundary of the object based on a shape of the expanded polygon when it is determined that at each location outside of, and adjacent to, the polygon expanded according to steps (c) and (d), the discrete portion tested at step (c) is of second material.

2. The method as recited in claim 1, wherein $g_i(X)$ is determined according to the Expression $$g_i(X) = -\left(\frac{1}{2}\right)(X-M_i)^T \overset{-1}{\underset{i}{\Sigma}} (X-M_i) - \left(\frac{1}{2}\right)\log\left|\underset{i}{\Sigma}\right| + \log(P_i)$$

where,

X=vector X, $M_i$=vector of the mean property, $\Sigma_i$=matrix of covariances for features in class i, $\Sigma_i^{-1}$=inverse matrix of matrix $\Sigma_i$, $|\Sigma_i|$=determinant of a covariance matrix, T=transpose of a resulting vector, P(i)=a priori probability that class i is observed.

3. The method as recited in claim 1, wherein $g_j(X)$ is determined according to the Expression $$g_j(X) = -\left(\frac{1}{2}\right)(X-M_j)^T \overset{-1}{\underset{j}{\Sigma}} (X-M_j) - \left(\frac{1}{2}\right)\log\left|\underset{j}{\Sigma}\right| + \log(P_j)$$

where,

X=vector X, $M_j$=vector of the mean property, $\Sigma_j$=matrix of covariances for features in class j, $\Sigma_j^{-1}$=inverse matrix of matrix $\Sigma_j$, $|\Sigma_j|$=determinant of a covariance matrix, T=transpose of a resulting vector, P(j)=a priori probability that class j is observed.

4. An autocontouring method, comprising the steps of:

(a) producing a two-dimensional image of a structure with the structure having at least one object disposed therein and the object is substantially defined by boundary, with an area within the boundary being of a first class of material and an area outside of the boundary being of a second class of material;

(b) forming a polygon in the object such that the polygon is fully within the boundary of the object and polygon subtends only a first class of material;

(c) testing an discrete portion of an area outside of, but adjacent to, the polygon according to a maximum a posteriori decision method according to an Expression if $P(i|X) > P(j|X)$, decide class i, else decide class j where, P(i|X)=probability that class i is a correct class for observation X, P(j|X)=probability that class j is a correct class for observation X, (d) expanding the polygon to include the discrete portion tested at step (c) if it is determined that the discrete portion is of a first class of material;

(e) repeating steps (c) and (d) until the testing at step (c) determine that at each location outside of, and adjacent to, a polygon expanded according to steps (c) and (d), a discrete portion tested at step (c) is of second material; and (f) computing a boundary of the object based on a shape of the expanded polygon when it is determined that at each location outside of, and adjacent to, the polygon expanded according to steps (c) and (d), the discrete portion tested at step (c) is of second material.

5. The method as recited in claim 4, wherein P(i|X) is determined according to an Expression $$P(i|X) = \frac{p(X|i)P(i)}{\sum_k p(X|k)P(k)}$$

where,

P(i|X)=probability of observing class i given vector X, p(X|i)=probability of observing vector X given class i, $\Sigma_k p(X|k)P(k)$=sum over all classes k of products of a probability density of data vector X given class k and an a priori probability of observing class k, P(i)=a priori probability that class i is observed, P(j)=a priori probability that class j is observed.

6. The method as recited in claim 4, wherein P(j|X) is determined according to an Expression $$P(j|X) = \frac{p(X|j)P(j)}{\sum_k p(X|k)P(k)}$$

where,

P(j|X)=probability of observing class j given vector X, p(X|j)=probability of observing vector X given class j, $\Sigma_k p(X|k)P(k)$=sum over all classes k of products of a probability density of data vector X given class k and an a priori probability of observing class k, P(j)=a priori probability that class j is observed.

* * * * *